United States Patent
Sethuraman et al.

(10) Patent No.: US 10,660,615 B2
(45) Date of Patent: May 26, 2020

(54) PATIENT-SPECIFIC ULTRASOUND THERMAL STRAIN-TO-TEMPERATURE CALIBRATION

(71) Applicant: KONINKLIJKE PHILIPS N.V., Eindhoven (NL)

(72) Inventors: Shriram Sethuraman, Cambridge, MA (US); Ajay Anand, Cambridge, MA (US); William Tao Shi, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 391 days.

(21) Appl. No.: 15/540,792

(22) PCT Filed: Dec. 17, 2015

(86) PCT No.: PCT/IB2015/059709
§ 371 (c)(1),
(2) Date: Jun. 29, 2017

(87) PCT Pub. No.: WO2016/108128
PCT Pub. Date: Jul. 7, 2016

(65) Prior Publication Data
US 2017/0360407 A1    Dec. 21, 2017

Related U.S. Application Data

(60) Provisional application No. 62/097,785, filed on Dec. 30, 2014.

(51) Int. Cl.
*A61B 8/08*    (2006.01)
*A61N 7/02*    (2006.01)
(Continued)

(52) U.S. Cl.
CPC ............... *A61B 8/485* (2013.01); *A61B 8/58* (2013.01); *A61N 7/00* (2013.01); *A61N 7/02* (2013.01); *A61B 8/085* (2013.01); *A61B 8/12* (2013.01)

(58) Field of Classification Search
CPC ...................................... A61B 8/485
See application file for complete search history.

(56) References Cited

U.S. PATENT DOCUMENTS

2007/0060847 A1*  3/2007  Leo ............. A61B 5/0084
                                          600/587
2007/0083195 A1   4/2007  Werneth et al.
(Continued)

FOREIGN PATENT DOCUMENTS

WO    2014076621 A1    5/2014

OTHER PUBLICATIONS

Seip, Ralf et al, "Non Invasive Estimation of Tissue Temperature Response to Heating Fields using Diagnostic Ultrasound", IEEE Trans. Biomed. Eng. 42, 828-839 (1995).
(Continued)

*Primary Examiner* — Rochelle D Turchen

(57) ABSTRACT

An apparatus for deriving tissue temperature from thermal strain includes a thermal strain measuring module. The module uses ultrasound (156, 158) to measure thermal strain in a region, within a subject, that surrounds a location (166a, 166f) where a temperature sensor is disposed. Also included is a temperature measurement module configured for, via the sensor, measuring a temperature at the sensor while the sensor is inside the subject. Further included is a patient-specific thermal-strain-to-temperature-change proportionality calibration module. The calibration module is configured for calibrating (S238) a coefficient and for doing so based on a measurement of a temperature parameter at that location derived from output of the temperature measurement mod-
(Continued)

ule and on a measurement of thermal strain at that location obtained via the strain measuring module. The coefficient is usable, in conjunction with a thermal strain measurement derived from another location within the region, in evaluating (S242), for that other location, another temperature parameter.

13 Claims, 3 Drawing Sheets

(51) Int. Cl.
 *A61B 8/00* (2006.01)
 *A61N 7/00* (2006.01)
 *A61B 8/12* (2006.01)

(56) References Cited

U.S. PATENT DOCUMENTS

2007/0106157 A1* 5/2007 Kaczkowski .......... A61B 5/015
 600/438
2013/0066584 A1 3/2013 Lan
2013/0204240 A1 8/2013 McCarthy
2015/0073400 A1* 3/2015 Sverdlik ................ A61N 7/022
 606/28
2016/0131540 A1 5/2016 Anand
2016/0346031 A1 12/2016 Anand

OTHER PUBLICATIONS

Varghese, T. et al "Ultrasound Monitoring of Temperature Change during Radiofrequency Ablation: Preliminary In-Vivo Results", Ultrasound in Medicient and Biology, vol. 28, No. 3, pp. 321-329, 2002.

Varghese, T. et al, "Real-Time Calibration of Temperature Estimates During Radiofrequency Ablation", Ultrasonic Imaging, vol. 26, pp. 185-200, 2004.

* cited by examiner

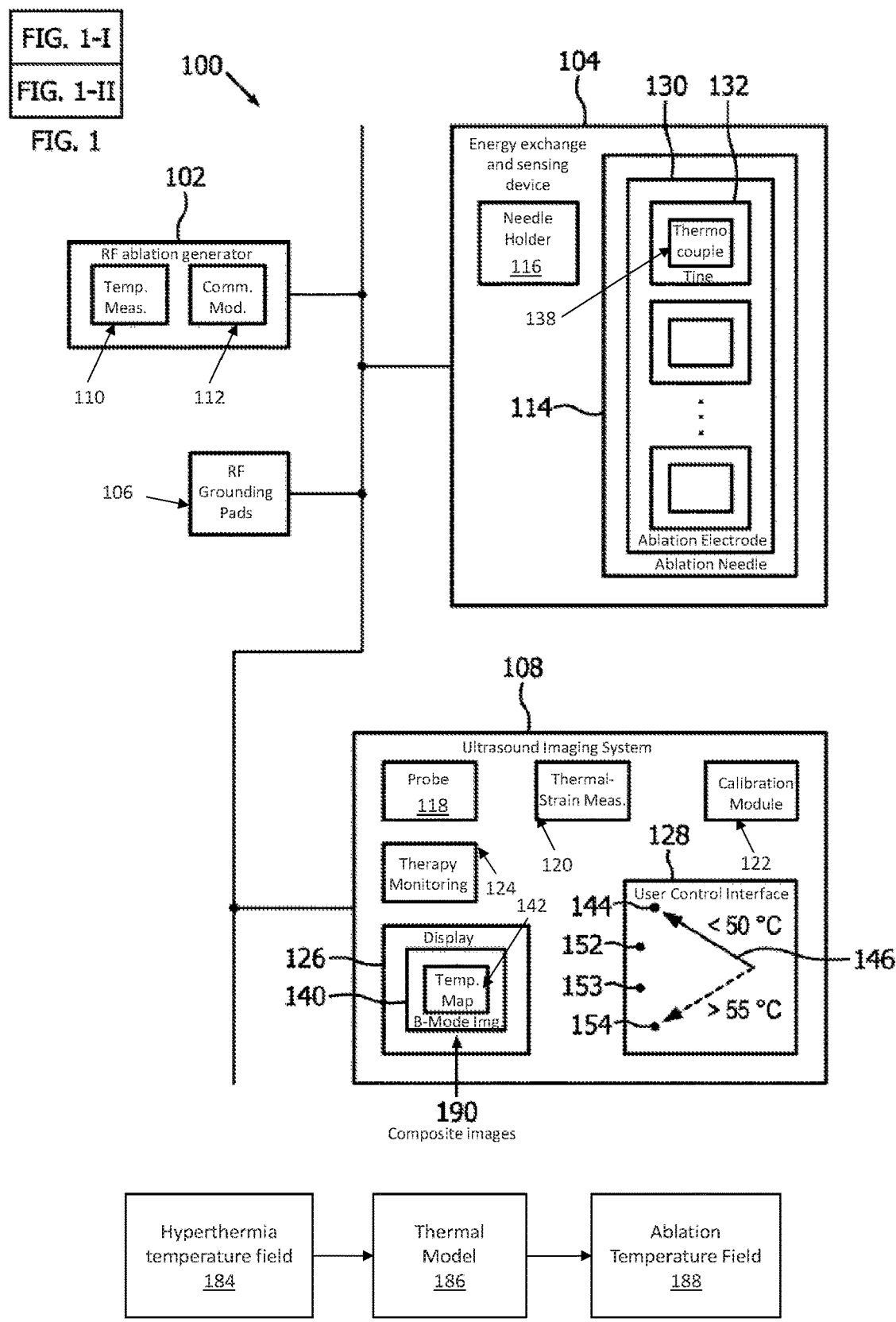
FIG. 1-I

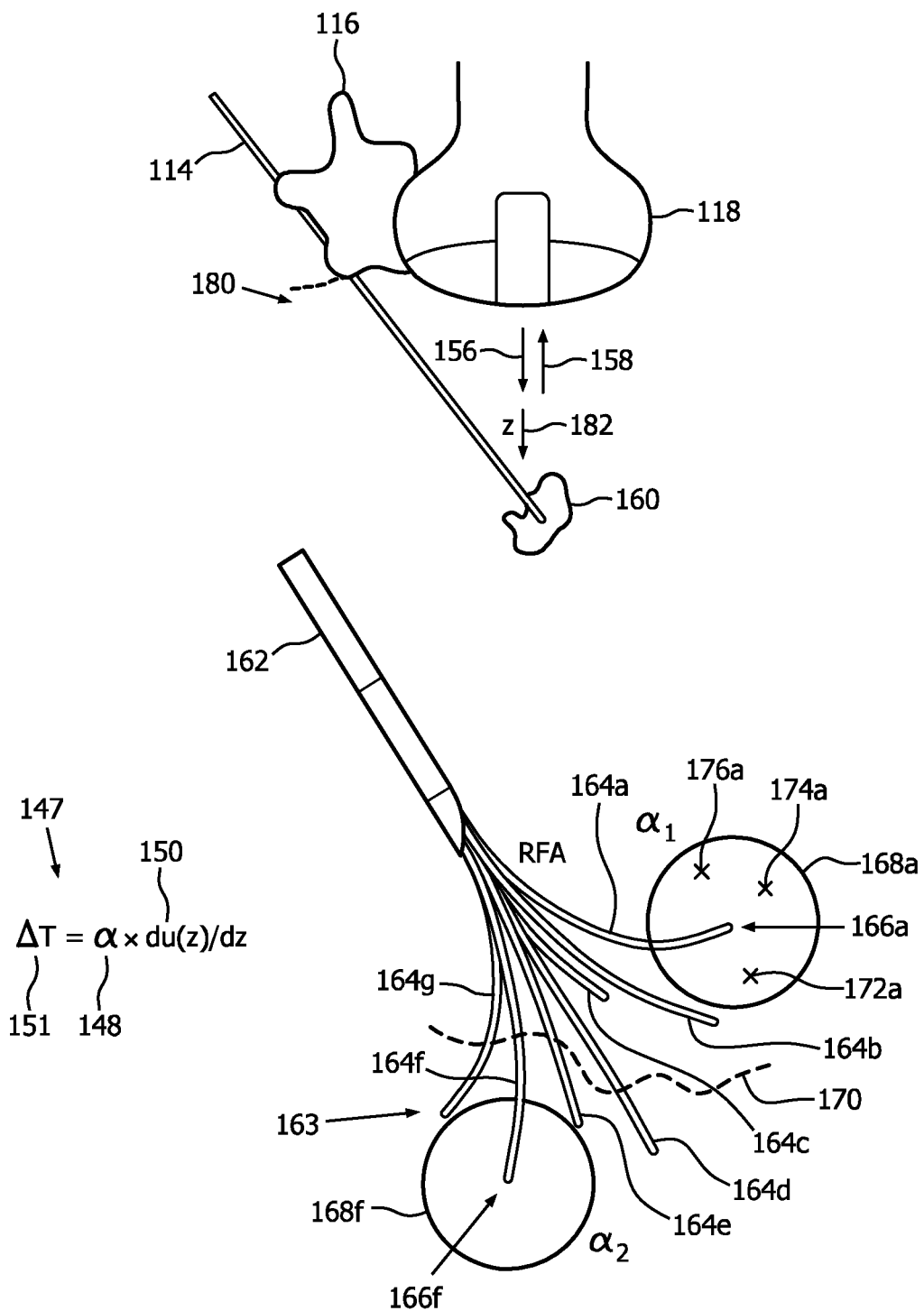
FIG. 1-II

PATIENT-SPECIFIC ULTRASOUND THERMAL STRAIN-TO-TEMPERATURE CALIBRATION

CROSS-REFERENCE TO PRIOR APPLICATIONS

This application is the U.S. National Phase application under 35 U.S.C. § 371 of International Application No. PCT/IB2015/059709, filed on Dec. 17, 2015, which claims the benefit of U.S. Provisional Application No. 62/097,785, filed Dec. 30, 2014. These applications are hereby incorporated by reference herein, for all purposes.

FIELD OF THE INVENTION

The present invention relates to using ultrasound thermal strain measurements to determine temperature and, more particularly, to such use in conjunction with a thermal sensor utilized internally.

BACKGROUND OF THE INVENTION

Thermal ablation techniques are an excellent alternative to major surgery, which can pose a risk even with the most experienced surgeon. These techniques are minimally invasive, requiring only needles (radiofrequency (RF), cryotherapy and microwave ablation) or a non-invasive heat source such as by using ultrasound, e.g., high-intensity focused ultrasound (HIFU). In most of the procedures, the cancerous tissue is heated to above 60° Celsius (C) and subject to necrosis.

Radiofrequency ablation (RFA) is currently the only FDA approved minimally invasive heating therapy in the United States. RF ablation uses a probe with an active electrode tip through which a 460-500 kilohertz (KHz) alternating current is conducted. The current propagates through the body to the grounding pads placed either on the back or the thigh of the patient. The current causes ionic agitation and frictional heating. Heat is then dissipated through thermal conduction to ablate the tumor. RFA is frequently used to treat liver cancer. There are about 500,000 new cases of metastatic liver cancer in the western world and about 1 million new cases for primary liver cancer worldwide (83% of which are in developing countries). RFA and microwave ablation therapies are also gaining tremendous popularity in China due to the large number of liver cancers reported (e.g., 433,000 new cases in 2009 alone). Current treatment protocols use the simplistic spherical ablation volume predicted from the device manufacturers' specifications. The actual treatment volumes greatly deviate from the prediction, resulting in large recurrence rates (approx. 35%).

RF ablation is typically performed under ultrasound, computed tomography (CT) or magnetic resonance imaging (MRI) guidance. Follow up is done with a CT scan or MRI within a month to assess effectiveness of ablation and again at 3 month intervals along with tumor markers to detect residual disease or recurrence. One common reason for the high recurrence rates is the inability to monitor and control ablation size to adequately kill the tumor cells. Real-time feedback is accordingly provided to the clinician by means of a temperature map of the ablated zone. This can currently be achieved with reasonable accuracy with MR based temperature imaging. However, MRI is expensive and may not be readily available. Ultrasound is another modality that is commonly used for image guidance during placement of the needle. Due to its ease of use and availability it is a preferred method for monitoring the lesions. However, the only way it is currently used for monitoring treatment is by visualizing the hyperechoic lesions on a B-mode image. Low contrast exists between normal and ablated tissue. Visual artifacts arise from gas bubbles. Thus, the visualization currently afforded by ultrasound is only approximate and not a good indicator of the treatment efficacy. Also reliance on gas bubbles for echogenicity encounters the problem that bubble formation mainly occurs at temperatures elevated above those needed for the ablation, potentially resulting in unnecessary cell damage and prolongation of the procedure.

Another proposed ultrasound technique for ablation monitoring is ultrasound thermometry. Ultrasound thermometry can potentially enable mapping the temperature distribution during thermal therapies in 3D spatial and temporal dimensions. Through the concept of thermal dose (derived from the time history of temperature rise), the extent of the ablation zone can be determined over the entire volume. Hence, ultrasound thermometry provides significant advantages over temperature measurements obtained from a single or a few thermocouples that provide only a sparse sampling of the ablation zone. The underlying principle of ultrasound thermometry is that the speed of sound in the tissue changes as a function of temperature which manifests as apparent shifts (displacement) in ultrasound echoes. The resulting temperature induced strain (derived by differentiating the displacement along the direction of the ultrasound beam) is nominally proportional to the temperature rise in the range up to 50° C. The proportionality constant (thermal strain to temperature coefficient) is typically estimated through a calibration performed in a water bath wherein a known temperature rise that produces the corresponding thermal strain is noted. One such study discloses calibration curves for different body tissue types. Varghese, T., Daniels, M. J., "Real-time calibration of temperature estimates during radiofrequency ablation", Ultrasonic Imaging, 26(3):185-200 (2004) (hereinafter "Varghese"). The curves, which each relate temperature rise to thermal strain, are each seen to be essentially linear over a hypothermia temperature range which extends up to 50° C. Accordingly, a proportionality constant can be derived for each tissue type. U.S. Patent Publication No. 2013/0204240 to McCarthy discloses an integrated catheter tip (ICT) that includes a thermocouple. The ICT is used for hyperthermia therapy. Readings from the thermocouple are used to measure temperature adjacent to the ICT. A radiometer is also used in the measurement, because heating is caused by microwave energy and because a more complete picture of the temperatures in the treatment region is desired.

SUMMARY OF THE INVENTION

The above-described Varghese method of proportionality factor calibration is feasible in laboratory studies and not in a clinical situation. Indeed, one could use calibration curves for a particular tissue type available from the literature. However, such values are only approximate with a high standard deviation arising from the difference in the method and local variations in the tissue composition. Even for a given tissue type, the temperature dependence of ultrasound propagation speed significantly varies, based on tissue composition, e.g., water content and fat content. The composition, for a given patient, can locally vary even within same organ such as the liver. Hence, for a given patient and subject an in situ estimate of the proportionality factor, i.e., the temperature-strain coefficient, affords greater accuracy in knowing the local temperatures throughout the intended ablation region 160. The accurately measured temperatures can be inputted into a thermal model to accurately predict temperatures in the ablation regime. For the in situ estimate, it is proposed herein below to obtain a reliable "ground truth" temperature value in vivo at the site of thermal treatment, as via a thermocouple onsite. The thermocouple may be at the tip of a tine of an RF ablation electrode. Applications of the inventive technology also extend to hyperthermia therapy. In McCarthy, for example, in which a thermocouple is used in hyperthermia therapy, ultrasound thermometry would offer an economical and safe alternative to microwaves for the regional temperature monitoring. Using the patient-specific coefficient proposed herein makes the ultrasound-thermometry-based monitoring more accurate.

In an aspect of what is proposed herein, an apparatus for deriving tissue temperature from thermal strain includes a thermal strain measuring module. The module uses ultrasound to measure thermal strain in a region, within a subject, that surrounds a location where a temperature sensor is disposed. Also included is a temperature measurement module configured for, via the sensor, measuring a temperature at the sensor while the sensor is inside the subject. Further included is a patient-specific thermal-strain-to-temperature-change proportionality calibration module. The calibration module is configured for calibrating a coefficient and for doing so based on a measurement of a temperature parameter at that location derived from output of the temperature measurement module and on a measurement of thermal strain at that location obtained via the strain measuring module. The coefficient is usable, in conjunction with a thermal strain measurement derived from another location within the region, in evaluating, for that other location, another temperature parameter.

In the ablation context and operationally, the clinician performs a test shot or heating to a few degrees and ultrasound data is collected. Ultrasound strain estimates are obtained over the entire intended ablation region, and the patient specific coefficient is determined. With this coefficient, temperature estimates are obtained over the region. Since the normal temperature of the human body is 37° C., the temperature estimates are below 50° C., i.e., in the hyperthermia range. A model is now used to predict temperatures in the ablative range. The input to the model is ultrasound determined temperature estimates, and ablation device parameters like power and impedance. The model is then run with various combinations of thermal conductivities and electrical conductivities. This is done as an optimization to best match an output temperature distribution with that obtained by the test shot. The optimization operates on the equations below:

$$\nabla \cdot [\sigma \nabla V] =$$
$$0 \text{ (assume } \sigma \text{ is independent of temperature)} \rightarrow (\sigma \nabla^2 V) = 0$$
$$\rho C \frac{dT}{dt} = \nabla \cdot (k \nabla T) + \sigma |\nabla V|^2$$

where k is the thermal conductivity, p is the density, C is the specific heat, $\sigma$ is the electrical conductivity.

The model is then re-initialized with the determined k and $\sigma$ and run with these values to predict ablative temperatures. The above test shot and subsequent model initialization procedure can be completed in 3-4 minutes. Now the clinician is ready to begin the ablation procedure. In this mode, as the therapy progresses, real-time power and impedance profiles are passed on to the model from the ablation generator. These profiles are part of a database of various temperature profiles with different values of electrical conductivity and thermal conductivity, the profiles having been generated a priori, even before the patient is on the table. Each of the profiles pertains to a particular output power of the RF ablation generator and impedance in the electrical flow from the RF ablation generator, through the electrode and onto the pads in completing the circuit. The profile links the output power and impedance to temperature increments throughout the region. The model calculates the current ablation temperature throughout a three-dimensional (3D) volume at each time step for the power and impedance input from the generator, and a thermal dose contour progresses as the therapy progresses. This progression is visualized on the screen in real-time. At the discretion of the clinician, or via automatic image matching to the intended ablation region, the therapy is stopped as the contour covers the tumor boundary with a margin. A more complex model could have heterogeneous zones of k and $\sigma$ and not just one k and $\sigma$ for the entire tissue. An example of a thermal model is provided in commonly-owned International Publication No. WO 2014/076621 to Anand et al.

Details of the novel technology for patient-specific ultrasound thermal strain to temperature coefficient calibration are set forth further below, with the aid of the following drawings, which are not drawn to scale.

BRIEF DESCRIPTION OF THE DRAWING

FIG. 1 is a schematic and conceptual diagram exemplary of patient-specific ultrasound thermal strain to temperature coefficient calibration in accordance with the present invention.

DETAILED DESCRIPTION OF EMBODIMENTS

Figure 2:
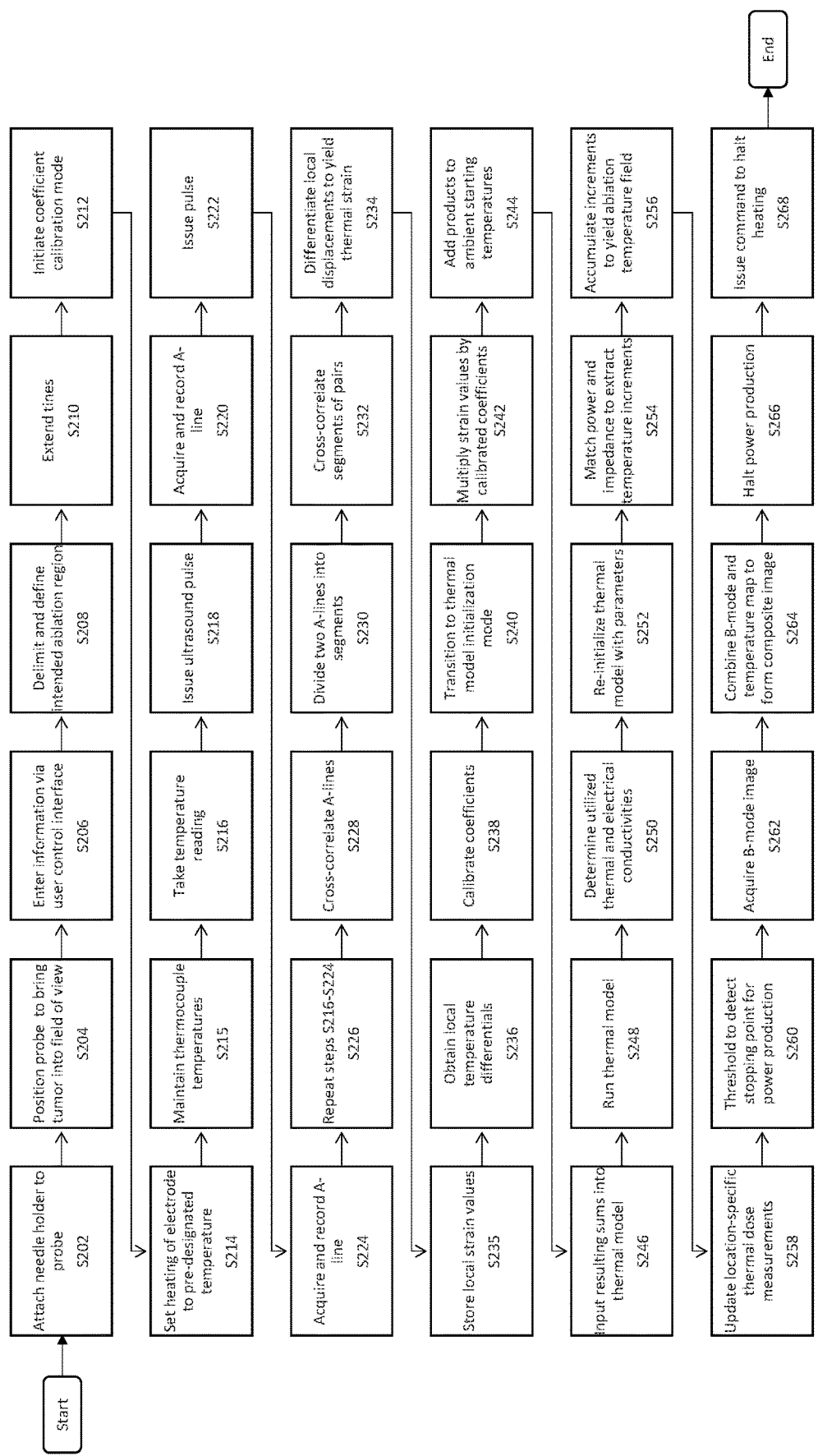
FIG. 2 is flow chart of a particular variation on methodology performable with the structures shown in FIG. 1.

FIG. depicts, by illustrative and non-limitative example, an apparatus 100 for deriving tissue temperature from thermal strain. The apparatus 100 includes an RF ablation generator 102, and energy exchange and sensing device 104, RF grounding pads 106, and an ultrasound imaging system 108.

The RF ablation generator 102 includes a temperature measurement module 110 and a communication module 112.

The energy exchange and sensing device 104 includes an ablation needle 114 and a needle holder 116.

Included in the ultrasound imaging system 108 are an ultrasound imaging probe 118, a thermal-strain measuring module 120, a patient-specific thermal-strain-to-temperature-change proportionality calibration module 122, a therapy monitoring module 124, a display 126, and a user control interface 128.

An RF ablation electrode 130 is incorporated within the ablation needle 114 and comprises one or more tines 132. Each tine 132 has, at a distal end, a tip. Offset slightly in from the tip is a thermocouple 138 or other thermal sensor.

All of the modules, and other data processing elements, may be implemented in any known and suitable combination of hardware, software and/or firmware.

Also, instead of an ablation needle, a catheter may deliver the electrode 130.

In addition, instead of an electrode for ablation, another ablation technique that uses internal temperature sensors may be employed, such as microwave ablation via microwaves delivered by the energy exchange and sensing device 104.

Non-ablation applications such as hyperthermia-based therapy in which ultrasound thermometry is used to monitor temperature are also within the intended scope of what is proposed herein.

The imaging probe 118 may be trans-thoracic and an internal probe such as a transesophageal echocardiography (TEE) probe.

Shown on the display 126 in FIG. 1 for illustrative purposes is a B-mode ultrasound image 140. Overlaid on the image 140 is a temperature map 142.

The apparatus 100 is operable in an coefficient calibration mode 144 (conceptually depicted in conjunction with a switchable arrow 146 in FIG. 1) to, as shown by the formula 147, calibrate a patient-specific ultrasound thermal strain to temperature coefficient 148 which serves as a proportionality factor between a thermal strain 150 and a temperature differential 151. The calibrated coefficient 148 may be obtained by dividing the temperature differential 151 by the thermal strain 150. In coefficient calibration mode 144, the RF ablation generator 102 is operated at a low power, keeping the temperature in the tissue below 50° C. It may be kept at 43° C., for instance, or in a range of 37° C. to 43° C.

This is followed by a hyperthermia temperature-field determination mode 152. In this mode 152, the calibrated coefficient 148 is applied to thermal strain 150 that has been calculated for locations throughout the intended ablation region.

A thermal model initialization mode 153 uses the determined temperature field and ablation device parameters to initialize the model for tissue properties discernable from comparing the temperature field to output temperatures of the model.

The apparatus 100 is also operable in a body tissue ablation and concurrent model execution mode, or "tissue ablation mode", 154 in which the RF ablation generator 102 is operated at a higher power, for ablation. The tissue is heated to above 55° C. and typically above 60° C. The model also operates ongoingly in the tissue ablation mode 154. Ablation therapy is performed on a human, or animal, patient.

Pulses 156 of ultrasound are emitted in the coefficient calibration mode 144, and the return pulses 158 are analyzed to assess thermal strain in the intended ablation region 160. Measurements of thermal strain 150 in the coefficient calibration mode 144 are taken at the thermocouples 138, e.g., within a radius centered at the thermocouple of twice an ultrasonic spatial resolution (lateral or axial) of the apparatus 110, and are used to calibrate the coefficient 148.

For an ablation needle 162, each of one or more tines 164a-g has at its distal end 163 a respective thermocouple 138.

Partially or fully surrounding a location 166a of the thermocouple 138 for the tine 164a is a volumetric region 168a to be associated with a particular calibrated coefficient 148 that is to be computed. Likewise as an example, FIG. 1 shows a second volumetric region 168f surrounding a location 166f of a respective thermocouple 138. Although the regions 168a, 168f are portrayed as spherical, they can be any arbitrary shape.

Although each region 168a, 168f is to be associated with a particular coefficient 148, the value of the coefficient when computed for each of two different regions may turn out to be the same. They can be the same or almost the same if the tissue composition in the immediate vicinity of both respective locations 166a, 166f is the same or almost the same. A hypothetical tissue-composition-based divider 170, which can actually be constructed by the user interactively onscreen, is shown in FIG. 1. Thus, the coefficient 148 can be expected to be calibrated to a different value for regions 168a on one side of the divider 170 than for the regions 168f on the other side of the divider.

Regions 168a, 168f may overlap. Even if, for example, regions 168a, 168f are truncated at the divider 170, regions on the same side of the divider may overlap. For the first region 168a, for instance, other than the surrounded or thermocouple location 166a, there is another location 172a, and there are additional locations 174a, 176a. When the temperatures at the additional locations 174a, 176a are estimated, i.e., in the hyperthermia temperature-field determination mode 152, the coefficient 148 for the first region 168a is utilized. However, if the other location 172a is also within the adjoining region (not shown), a selection can be made between the regions sharing the location, or a combination such as an average of respective coefficients 148 can be computed. The average may be weighted by distance of the location 172a to the respective thermocouple locations 166a, 166f or, in the case of selection, selection can be made of the based on the closest thermocouple location.

FIG. 2 is a flow chart exemplary of a procedure 200 for deriving tissue temperature from thermal strain 150. The procedure 200 is performed serially through the above-described modes 144, 152, 153, 154, transitioning mode-to-mode through the series automatically, without the need for user intervention. The needle holder 116 is attached fixedly to the probe 118 (step S202). With the needle holder 116 attached, the probe 118 is positioned manually or via motorized movement to bring the tumor to be ablated into the field of view of the probe (step S204). If the probe 118 has a 2D transducer array, the probe can, with the tumor within the field of view, be held motionless throughout the procedure 200, either manually or by the motorized mechanism, for ablation of all tumorous body tissue within the field of view. Cyclical body motion, such as respiratory or cardiac, can be automatically and dynamically compensated through a combination of motion gating and ultrasound speckle-based motion tracking. With the probe 118 in place, the needle 114 can be manually advanced through the needle holder 116 and into the subject 180 under operator control by a distance, and at an orientation, that are readable from the needle holder. For example, the proximal end of the needle 114 can have graded markings that show how far the needle has been advanced. This information is entered via the user control interface 128 (step S206). Accordingly, the tip of the needle 114 is at a known location in image space and is into or just short of the tumor. The clinician viewing the tumor interactively delimits and defines the intended ablation region 160 onscreen (step S208). Under operator control, the one or more tines 164a-g are extended (step S210). The tines 164a-g are stiff and extend invariantly into the body tissue, mainly or entirely tumorous, that is being pierced. Thus, the thermocouple locations 166a, 166f on the tines 164a-g and slightly offset from the tine tips are known. Alternatively, X-rays from a CT or fluoroscopy system registered to the ultrasound imaging system 108 can be employed to localize the locations 166a, 166f. The coefficient calibration mode 144 is then initiated (step S212). The RF ablation generator 102 is operated at a low power keeping the temperature in the tissue below 50° C. It may be kept at 43° C., for instance, or in a range of 37° C. to 43° C. The RF ablation generator 102, in effect, sets the heating of the electrode 130 to a pre-designated temperature, or temperature range, that is below the maximum temperature of, for example, 50° C. (step S214). Also, at this point, the RF generator begins self-checking the temperatures at all thermocouples 138 and regulates the temperatures ongoingly, in both the current coefficient calibration mode 144 and throughout the above-discussed ensuing modes 152-154. The thermocouple temperatures are thus maintained to whatever is the current set temperature or temperature range (step S215). A temperature reading is now taken by all thermocouples 138 at their respective locations 166a, 166f (step S216). An ultrasound pulse 156 is issued in a current direction in volumetric space (step S218). From a return echo pulse 158 in the same direction, an A-line is acquired and recorded (step S220). Then, steps S218 and S220 are repeated in each direction for the intended ablation region 160. In particular, a pulse 156 is issued (step S222) and an A-line is acquired and recorded (step S224). For a 2D ultrasound transducer array, the scan may proceed from an elevationally high row of scan lines progressively downward. Alternatively, a one-dimensional array can be pivoted mechanically for a similar scan. After the scan, the RF ablation generator then raises the temperature at the respective electrodes, and steps S216-S224 are repeated (step S226). The two A-lines of a current direction are cross-correlated (step S228). The resulting offset is used to divide the two A-lines into segments such that a segment of one A-line is paired with what is, in view of the offset, a spatially close segment of the other A-line (step S230). Segments of a pair are cross-correlated to fine tune the global offset to a local value, this being done for each pair (step S232). The local values are the apparent displacements usable in computing thermal strain 150. In particular, the local displacements are differentiated in the current, i.e., axial 182, direction to yield the local value of the thermal strain 150 (step S234). The local strain values are stored (step S235). The local temperature differentials 151 are obtained by subtracting the temperature read in step S216 from the temperature reading in step S227 for each thermocouple 138 (step S236). The coefficient(s) 148 are calibrated by, at the locations 166a, 166f of the thermocouples 138, respectively evaluating the formula 147 with the local temperature differential 151 and the local value of the thermal strain 150 (step S238). The apparatus 100 now transitions to the thermal model initialization mode 153 (step S240). The stored local strain values of all directions are respective multiplied by the calibrated coefficient 148 of the respective volumetric regions 168a, 168f, or, for locations 172a in region overlap, optionally by an averaged coefficient (step S242). The respective products, i.e., temperature differentials 151 that have been evaluated, are added to the corresponding, ambient starting temperatures, typically about 37° C., measured in step S216 (step S244). The resulting sums for the associated locations 172a constitute a hyperthermia temperature field 184 that, in the thermal model initialization mode 153, is inputted into a thermal model 186 (step S246). The thermal model 186 is then run with various combinations of thermal conductivities and electrical conductivities (step S248). For the best match of the temperature field with the model-generated temperature field, the utilized thermal and electrical conductivities are determined (step S250). The model 186 is re-initialized with these two parameters (step S252). In the case of a model for liver tissue, typical model parameters are, for instance, an electrical conductivity of 0.148 Siemens per meter (S/m), a thermal conductivity of 0.465 watts per meter Celsius (W/mC), a density of 1060 kilograms per cubic meter (kg/m$^3$), a heat capacity of 3600 joules per kilogram Celsius (J/Ckg) and a perfusion rate of 6.4×10$^{-3}$/second.

In the tissue ablation mode 154, real-time power and impedance profiles from the RF ablation generator 102 are time-step by time-step matched to current power and impedance values during ablation to extract respective temperature increments (step S254). The increments are accumulated to yield in real time an ablation temperature field 188 (step S256). Location-specific thermal dose measurements are ongoingly updated (step S258). These measurements and/or current ablation temperatures can be thresholded to detect a stopping point for power production by the RF ablation generator 102 (step S260). Thus, based on the calibrated coefficient 148, monitoring is performed, during the provision of therapy, of temperature at one or more additional locations 174a, 176a within the region 168a, 168f. Alternatively or in addition to the thresholding, one or more B-mode images 140 are acquired (step S262) and color-coded temperature maps 142 corresponding to the real-time ablation temperature field 188 are overlaid over, or otherwise combined (e.g., alpha blended) with, the B-mode image(s) to form respective composite images 190 (step S264). The clinician may accordingly visually judge when a stopping point for the heating has been reached and thus, via the user control interface 128, halt power production by the RF ablation generator 102 (step S266). Whether stopping is automatic or operator-initiated, the ultrasound imaging system 108 issues a command to the RF ablation generator 102 to halt heating via the RF ablation electrode 130 since ablation is now complete (step S268).

While the invention has been illustrated and described in detail in the drawings and foregoing description, such illustration and description are to be considered illustrative or exemplary and not restrictive; the invention is not limited to the disclosed embodiments.

For example, instead of an overlaid temperature map, the map is displayable alongside the B-mode image.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus for deriving tissue temperature from thermal strain, comprising:
an ultrasound imaging probe;
a thermal-strain measuring module configured for using ultrasound, via said probe, to measure thermal strain in a region, within a subject, that surrounds a location where a temperature sensor is disposed inside said subject, wherein the temperature sensor is configured to measure a temperature; and
a patient-specific thermal-strain-to-temperature-change proportionality calibration module configured for calibrating a coefficient, said calibrating being based on a measurement of a temperature parameter at said location derived from output of said temperature sensor and on a measurement of thermal strain at said location obtained via said strain measuring module, wherein said calibrating entails dividing said measurement of the temperature parameter by said measurement of thermal strain,
wherein the apparatus is configured for using said calibrated coefficient in conjunction with a thermal strain measurement derived from another location within said region, in evaluating, for said another location, another temperature parameter, and
wherein the apparatus is (i) configured for inputting, into a thermal model, said another temperature parameter and, based on output from said model, determining a current ablation temperature at said another location, and/or (ii) configured for monitoring heating in said region and basing said monitoring on said measurement of thermal strain and on the calibrated coefficient.

2. The apparatus of claim 1, comprising a therapy delivery device configured for heating the surrounded location.

3. The apparatus of claim 2, said therapy delivery device incorporating said temperature sensor and being configured to deliver therapy to said subject.

4. The apparatus of claim 3, said therapy delivery device comprising a radiofrequency ablation electrode having a tine that has an end at which said sensor is disposed.

5. The apparatus of claim 1, the monitoring operating on a plurality of locations, in said region, other than said another location and the surrounded location and being based on the calibrated coefficient as a fixed parameter being applied for the plural locations.

6. The apparatus of claim 5, comprising a therapy delivery device comprising said temperature sensor, said region being a first region, said therapy delivery device further comprising a second temperature sensor and being configured for concurrently monitoring heating in said first region and in a second region, within said subject, that surrounds said second temperature sensor, said apparatus being further configured for calibrating a second coefficient for said second region.

7. The apparatus of claim 5, further comprising a display to depict simultaneously, via said display, both a map representative of temperature rise at the plural locations and an ultrasound image encompassing said plural locations, said apparatus being further configured for calculating said temperature rise based on the calibrated coefficient.

8. The apparatus of claim 7, said depicting showing said map and said image in overlapping registration.

9. The apparatus of claim 1, comprising a therapy delivery device and configured with a coefficient calibration operating mode in which heating by said device results in a temperature at the sensor location that is kept below a maximum temperature that is below 50 degrees centigrade, said mode being operable for said using, said measuring, and said calibrating.

10. The apparatus of claim 9, comprising a therapy monitoring module, said apparatus being configured with a body tissue ablation mode in which heating by said device results in a temperature at the sensor location that is maintained above a minimum temperature that is above 55 degrees centigrade, said therapy monitoring module being configured for, in the ablation mode heating, operating based on the calibrated coefficient.

11. The apparatus of claim 1, wherein said another temperature parameter is a temperature differential.

12. The apparatus of claim 1, said using ultrasound comprising:
emitting ultrasound; cross-correlating resulting echoes to calculate thermally induced apparent displacements in tissue of said region; and, to make said measurement of thermal strain at the surrounded location, finding, in an axial direction of the emitted ultrasound, a rate of change of respective ones of said displacements.

13. A computer readable medium embodying a program for patient-specific thermal-strain-to-temperature-change proportionality calibration, said program having instructions executable by a processor for performing a plurality of acts, from among said plurality there being the acts of:
using ultrasound to measure thermal strain in a region, within a therapy subject, that surrounds a location where a temperature sensor is disposed;
measuring a temperature at said sensor while said sensor is inside said subject; and
based on a measurement of a temperature parameter at said location and on a measurement of thermal strain at said location, calibrating a coefficient usable, in conjunction with a thermal strain measurement derived from another location within said region, in evaluating, for said another location, another temperature parameter, wherein said calibrating entails dividing said measurement of the temperature parameter by said measurement of thermal strain.

* * * * *